United States Patent [19]

Shinnar

[11] Patent Number: 5,471,991
[45] Date of Patent: Dec. 5, 1995

[54] WAVELET ANALYSIS OF FRACTAL SYSTEMS

[75] Inventor: Meir Shinnar, Bala Cynwyd, Pa.

[73] Assignee: Trustees of the University of Pennsylvania, Philadelphia, Pa.

[21] Appl. No.: 152,526

[22] Filed: Nov. 16, 1993

[51] Int. Cl.⁶ .................................................. A61B 5/0452
[52] U.S. Cl. .................................................. 128/705
[58] Field of Search .................................... 128/696, 702, 128/703, 705, 706, 708; 382/56, 41

[56] References Cited

U.S. PATENT DOCUMENTS

| | | | |
|---|---|---|---|
| 4,422,459 | 12/1983 | Simson | 128/702 |
| 4,941,193 | 7/1990 | Barnsley et al. | 382/56 |
| 5,046,504 | 9/1991 | Albert et al. | 128/696 |
| 5,201,321 | 4/1993 | Fulton | 128/702 |
| 5,217,021 | 6/1993 | Steinhaus et al. | 128/702 |

OTHER PUBLICATIONS

Argoul, et al., "Wavelet Analysis of Turbulence Reveals the Multifractal Nature of the Richardson Cascade", Nature, vol. 338, pp. 51–53, Mar. 2, 1989.

Arneodo, et al., "Wavelet Transform Analysis of Invariant Measures of Some Dynamical Systems", Text: "Wavelets: Time, Frequency, Methods & Phase Space", Ed. J. Combes, A. Grossman and P. Tchamitchian, 1989, Springer Verlag.

Shinnar, et al., "Wavelet Analysis of ECGs", Nov. 11–14, 1991, Abstracts from the 64th Scientific Sessions.

Shinnar, et al., "Wavelets and the Multifractal Substrate of Ventricular Tachycardia", Nov. 16–19, 1992, Abstracts from the 65th Scientific Sessions, pp. I–319.

Tuteur, F. B., "Wavelet Transformations in Signal Detection", Text: "Wavelets: Time, Frequency, Methods & Phase Space", Ed. J. Combes, A. Grossman and P. Tchamitchian, 1989, Springer Verlag.

Primary Examiner—George Manuel
Attorney, Agent, or Firm—Woodcock Washburn Kurtz Mackiewicz & Norris

[57] ABSTRACT

System and method for determining characteristics of a system ideally represented by fractals by using wavelet analysis to determine whether regions of a signal derived from the fractal system are self affine, in particular, using wavelet analysis of an ECG signal to determine whether a patient is at risk for ventricular tachycardia or sudden death.

10 Claims, 6 Drawing Sheets

WAVELET ANALYSIS OF FRACTAL SYSTEMS

BACKGROUND OF THE INVENTION

1. Field of the Invention

The present invention is related to a method and system for using wavelet analysis to evaluate a signal generated by a fractal system and more particularly to a method and system for evaluating an Electrocardiogram ("ECG") signal to detect persons having heart disease or those who are at risk for ventricular tachycardia ("VT") or sudden death.

2. Description of the Prior Art

It is known that some systems are ideally comprised of fractals. Fractals are geometric shapes whose structure is such that magnification by a given factor reproduces the original object. However, if such a system also comprises and multifractals, the system may contain abnormalities in its fractal structure which are indicative of problems in the system.

For example, the conduction system of a healthy human heart is considered to be comprised of fractals where fractal systems have the same dimension and scaling law throughout. In a multifractal system the scaling law is different at different points. Since the conduction system of the human heart is comprised of fractals, the system should have the same dimension and scaling law throughout. Indeed, the most common substrate for ventricular tachycardia after a myocardial infarction is a local scar, which should have a multifractal structure. The substrate for ventricular tachycardia has been thought to have increased dispersion of refractoriness where this increased dispersion can lead to the possibility of the electrical signal entering reentrant loops, which lead to ventricular tachycardia or sudden death. Thus, to evaluate whether a human heart is considered to be healthy, the fractal system could be evaluated to determine if it includes multifractals. It is difficult, however, to determine whether a system is a non-ideal fractal system, i.e., comprised of fractal and multifractals. As a consequence, other techniques have been developed to evaluate signals produced by non-ideal fractal systems.

In particular, systems and methods have been developed to evaluate particular regions of an ECG signal using filtering techniques. It has been found that certain frequency characteristics in an electrocardiogram ("ECG") signal may indicate the presence of late potentials ("LP"). It has been found that by evaluating the portion of an ECG immediately following the Q, R, and S waves ("QRS") (also known as the ventricular depolarization complex) for the presence of particular high frequency components, LPs could be determined in certain patients. Such a technique is described in U.S. Pat. No. 4,422,459 to Simson, which is hereby incorporated by reference. Another technique uses a moving, short window FFT to analyze an ECG signal for diagnostic purposes. Such a technique is described in U.S. Pat. No. 5,046,504 to Albert et al., which is also hereby incorporated by reference. Unfortunately, known techniques have not been found effective at detecting the presence of all types of heart disease or patients at risk for VT or sudden death. Instead, existing techniques generally focus on detecting the presence of LPs.

Accordingly, present invention is designed to permit a more rigorous evaluation of signals from fractal systems, such as the conduction system of the heart, so that additional characteristics of the system may be recognized and diagnosed.

SUMMARY OF THE INVENTION

The present invention is directed to systems and methods for determining characteristics of a signal derived from a system comprised by fractals by using wavelet analysis to determine whether regions of the signal derived from the fractal system are self affine. In particular, a method of the present invention evaluates characteristics of a signal derived from a fractal system. The method first selects a region of the signal for analysis which is known to be self affine. Then the method performs wavelet analysis of the selected region to determine whether the region is indeed self affine during normal operation of the fractal system and then determines the characteristics of the fractal system as a function of whether the selected region is self affine.

In another embodiment of the present invention, a method analyzes an electrocardiogram ("ECG") signal to determine whether a patient is at risk for ventricular tachycardia or sudden death. The method first selects a region of the ECG signal for analysis. The method performs wavelet analysis of the selected region of the ECG signal to determine whether the region is substantially self affine and exhibits no abnormalities or whether the region is not substantially self affine and exhibits abnormalities. Then, the method compares a result of the wavelet analysis to a predetermined threshold to determine whether the selected region of the signal exhibits an abnormality representative of a risk for ventricular tachycardia or sudden death.

In another preferred embodiment of the invention, the method determines whether a patient is at risk for ventricular tachycardia or sudden death. The method uses an electrocardiograph to generate an electrocardiogram ("ECG") signal of the patient and selects a region of the ECG signal for analysis. The method performs wavelet analysis of the selected region of the ECG signal to determine whether the region is substantially self affine and exhibits no abnormalities or whether the region is not substantially self affine and exhibits abnormalities. Then the method compares a result of the wavelet analysis to a predetermined threshold to determine whether the selected region of the signal exhibits an abnormality representative of a risk for ventricular tachycardia or sudden death.

In another preferred embodiment, a system evaluates characteristics of a signal derived from a fractal system. The system includes a wavelet analysis system adapted to select a region of the signal for analysis which is generally self affine. The wavelet analysis system is also adapted to perform wavelet analysis of the selected region to determine whether the region is indeed self affine during normal operation of the fractal system and to determine the characteristics of the fractal system as a function of whether the selected region is self affine. Finally, the system also includes means for indicating an output of the analysis system to an operator for an evaluation of the characteristics.

In another preferred embodiment, a system determines whether a patient is at risk for ventricular tachycardia or sudden death. The system includes an electrocardiograph adapted to generate an electrocardiogram ("ECG") signal of the patient and a computer system adapted to select a region of the ECG signal for analysis. The computer system is also adapted to perform wavelet analysis of the selected region of the ECG signal to determine whether the region is substantially self affine and exhibits no abnormalities or whether the region is not substantially self affine and exhibits abnormalities and to compare a result of the wavelet analysis to a standard indicative of a normal ECG to determine whether the selected region of the signal exhibits an abnormality representative of a risk for ventricular tachycardia or sudden death.

BRIEF DESCRIPTION OF THE DRAWINGS

The above and other aspects and advantages of the invention will become more apparent from the following detailed description of the presently preferred exemplary embodiment of the invention taken in conjunction with the accompanying drawings, of which.

DETAILED DESCRIPTION OF PREFERRED EMBODIMENTS

Figure 1:
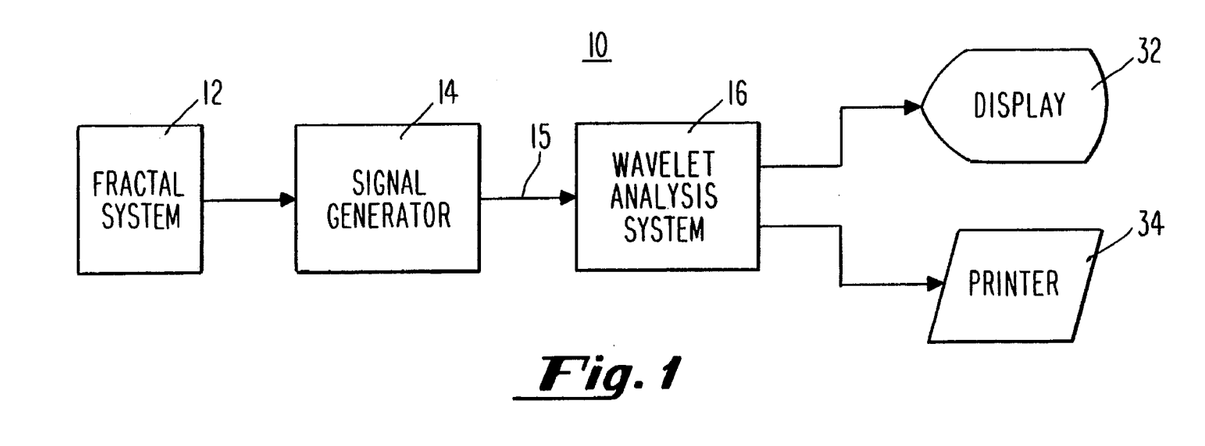
FIG. 1 is a block diagram of an exemplary system for analyzing a signal of a fractal system in accordance with the present invention.

FIG. 1 is a block diagram of an exemplary system 10 of the present invention. As shown in FIG. 1, the exemplary system 10 includes a fractal system 12 which is under analysis, a signal generator 14, a wavelet analysis system 16, a display 32, and a printer 34. In system 10, the signal derived from the fractal system 12 is evaluated to determine particular underlying characteristics of the fractal system 12. As noted above, the system 12 is deemed to be a fractal system if it is ideally comprised of fractals. The signal generator 14 generates a signal 15 derived from the fractal system 12. Signal 15 is then evaluated in accordance with the techniques of the invention to determine the characteristics of the fractal system 12.

Wavelet analysis system 16 processes the signal 15 generated by the signal generator 14 to determine the characteristics of the fractal system 12. The results are then displayed using a display 32 such as a cathode ray tube ("CRT"), liquid crystal display ("LCD") or video display or printed using a printer 34 such as laser printer, color plotter, or dot matrix printer. The characteristics displayed or printed may be a number or series of numbers or may be a plot representative of the characteristics determined by the wavelet analysis system 16.

In the exemplary embodiment of the present invention, the wavelet analysis system 16 determines the characteristics of the fractal system by determining whether particular or selected regions (time segments or points) of the signal 15 are self affine, i.e., whether these regions are locally self affine. The signals produced by such systems are known to have particular statistical properties. One such statistical property is that the signals should be self affine or self similar signals. Based on this property, a signal generated by a system which is ideally comprised by fractals can be evaluated to determine certain characteristics of the underlying system. In particular, the signal produced by such a system may be evaluated to determine if it is actually self affine across the signal or at particular locations within the system. This technique works especially well if the underlying system is not stationary, where a system is considered to be stationary if it is time invariant. If the signal is not self affine throughout the system or at particular locations, underlying characteristics of the signal generating system may be determined by evaluating the behavior of the signal at such locations. From the determination of whether particular regions are locally self affine, the wavelet analysis system 16 determines underlying characteristics or a quantitative parameter of the fractal system. The parameter is related to changes in the fractal structure of the fractal system 12. To determine whether the selected regions of the signal 15 are locally self affine, the wavelet analysis system uses particular properties of fractal systems, wavelets, and self affine signals. These properties are described below.

Wavelet analysis is used to decompose a signal by scale by translating and dilating an analyzing wavelet. It is known that a wavelet transform analyzes a signal according to scale rather than according to frequency. As known to those skilled in the art, ideal fractal systems and signals derived from the fractal system have the same scaling law throughout. Wavelet analysis can be used to determine whether the scaling law is consistent throughout the signal 15 using the property that a signal derived from an ideal fractal system is self affine. When a fractal system 12 is not ideally comprised of fractals but also includes multifractals, the scaling law relationship throughout the system 12 will break down and the signal 15 will not be self affine throughout. In this scenario, the signal 15 may only be self affine in particular regions (time segments or points) of the signal 15, i.e., locally self affine. Using these properties, wavelet analysis can be used to determine whether the signal 15 is self affine, whether the fractal system 12 is comprised of fractals or multifractals, and thereby determine characteristics of the fractal system 12.

In particular, if f(t) is the signal, and g(t) is an analyzing wavelet, then the wavelet analysis s(a,b) at a time b, and scale a, can be determined by:

$$s(a,b) = \int_{-\infty}^{\infty} f(t) g^*\left(\frac{t-b}{a}\right) \frac{1}{\sqrt{a}} \, dt \quad (1)$$

Equation 1 can be translated by substitution of variables to:

$$s(a,b) = \int_{-\infty}^{\infty} f(at+b) g^*(t) \sqrt{a} \, dt \quad (2)$$

It can be shown that with a suitable analyzing wavelet g(t), f(t) may be reconstructed from s(a,b). If f(t) is self affine throughout f(t), then f(t) will be statistically identical to $h^{-\alpha}f(ht)$ and f(ht) also statistically identical to $h^{+\alpha}f(t)$. Generally, the signal 15 (f(t)) is not self affine throughout. The signal 15 is, however, generally locally self affine, i.e., self affine at selected regions of the signal 15. A selected region of f(t+b) is considered to be locally self affine at the time b, if: (i) for t in an interval around 0, and, (ii) h in a range around 1, f(b+t) is statistically identical to $h^{-\alpha}f(b+ht)$. Substituting $a_1a_2$ for a in Equation 2 and the locally self affine relationship given above, it can be shown that $s(a_1a_2,b)$ is approximately equal to:

$$s(a_1a_2,b) = a_1{}^\alpha \sqrt{a_1} \int_{-\infty}^{\infty} f(a_2t+b)g^*(t) \sqrt{a_2}\, dt \quad (3)$$

and it can also be shown that:

$$s(a_1a_2,b) \approx a_1^{\alpha+\frac{1}{2}} s(a_2,b) \quad (4)$$

provided: (i) $a_1$ is in the range of scales where f(t) is self affine; and, (ii) g(t) is essentially equal to 0 outside the range where $f(a_2t)$ is self affine.

Using the relationship shown in equation 4, it can be shown that the log of the wavelet transform $s(a_1a_2,b)$ for self affine signals is be equal to the $\log(a_1^{\alpha+\frac{1}{2}}s(a_2,b))$ which is equal to $(\alpha+\frac{1}{2})(\log(a_1)+\log(s(a_2,b)))$. Thus, for selected scales $a_1a_2$, the plot of the log of the wavelet transform $s(a_1a_2,b)$ versus the log of the scale $a_1$ should have a slope of approximately $\alpha$. As a consequence, for a selected regions of f(t) (signal 15), if the region is locally self affine, the slope of the plot of the log of wavelet transform versus the log of the different scales $a_1$ should also be approximately $\alpha$, where $\alpha$ is a constant.

In addition, since fractal systems 12 should have the same scaling law throughout, the log of the wavelet transform versus the log of the scales of different regions should have the same slope throughout. In other words, the slope of the log of the wavelet transform for the different scales $a_1a_2$ should be approximately $\alpha$ for all the selected regions. If $\alpha$ varies as a function of the region or is not linear, the signal 15 is not self affine, the underlying fractal system 12 is not ideal, and it is determined that the system 12 is comprised of fractals and multifractals. The variation of the slope from region to region may be evaluated statistically, i.e., the variance or standard deviation may be determined or plotted, or the log of the wavelet transform versus the log of the scale $a_1$ versus the different regions may be plotted as shown in FIGS. 4–7.

Consequently, wavelet analysis can be used to determine whether selected regions of the signal 15 are self affine, and, based on this, the determination of the variance of the slope of the log of the wavelet transform versus the log of the scale for each region, a measure of the characteristics or fractal structure of the fractal system 12, can be determined by noting the variation of the determined slope across selected regions. The slope should be relatively constant for a signal 15 from a ideal fractal system 12, and should vary for a fractal system 12 comprised of fractals and multifractals. A preferred embodiment or application of the present invention is described with reference to FIGS. 2 and 3.

Figure 2:
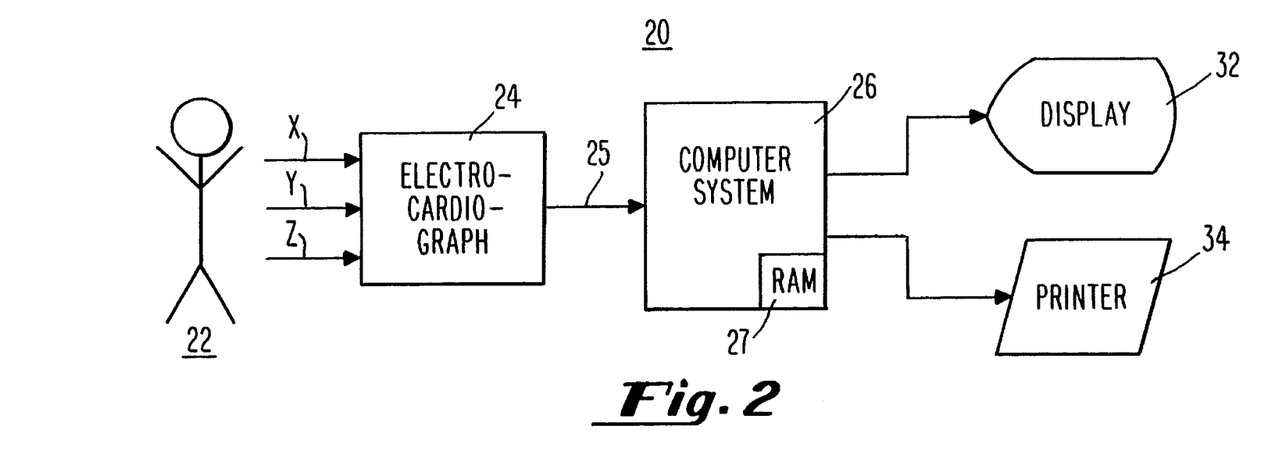
FIG. 2 is a block diagram of a preferred embodiment of the exemplary system for analyzing an ECG signal in accordance with the present invention.

FIG. 2 is a block diagram of a preferred embodiment or application of the present invention. As shown in FIG. 2, the present invention may be used to evaluate the a human being or patient 22, in particular, an electrocardiograph 24 is used to generate an ECG signal 25 which is derived from the conduction system of the heart of the patient 22. As known to those skilled in the art, the conduction system of the human heart is a fractal system. Disease in the heart is believed to cause a breakdown in the fractal structure of the heart and thus lead to a system comprised of fractals and multifractals. The present invention is ideally used to evaluate the ECG to determine a quantitative parameter which is related to changes in the fractal structure of the conduction of the electrical signal through the heart; i.e., it detects the presence of fractals and multifractals which indicates the presence of heart disease, a patient at risk for VT or sudden death, and the like. This is accomplished through wavelet analysis of the ECG to determine whether any abnormalities can be found other than late potentials evaluated using conventional methods, although the present invention can be used to evaluate late potentials as well. In particular, wavelet analysis is used to determine whether the scaling law is disrupted. An alteration in the scaling law reflects a disturbance in the fractal spread of activation in the myocardium in patients. In the present invention, the scaling law is determined to be disrupted if selected regions of the ECG signal 25 are not locally self affine.

The computer system 26 converts the ECG signal 25 to a digital signal, averages the ECG signal 25, and performs wavelet analysis of the averaged digital ECG signal. In the preferred embodiment of the invention, the computer system 26 includes an analog to digital converter, memory devices, such as random access memories (RAM) 27 and read only memories (ROM), and a processor. In addition, in the preferred embodiment of the present invention, the ECG signal 25 is averaged, although averaging of the ECG signal 25 is not required.

The ECG signal 25 itself may also be comprised of many different signals (such as twelve different signals) from a plurality of leads applied to the patient. In the preferred embodiment of the present invention, the ECG signal 25 is comprised of three common signals referred to in the art as X, Y, and Z. These X, Y, and Z signals are converted from analog to digital and averaged over many periods of the ECG signal 25 in accordance with known techniques.

Computer system 26 then performs wavelet analysis of the ECG signal 25 to determine whether the ECG signal exhibits abnormalities indicative of abnormalities in the conduction system of the heart of the patient 22. In particular, wavelet analysis is used to determine whether selected regions of the ECG signal 25 are self affine. Then, based on this determination, a measure of the characteristics of the fractal structure of the heart of the patient 22 is determined. In particular, variances in the slope of the log of the wavelet transform versus the log of scales across the selected regions of the ECG signal 25 are determined. The slope should be relatively constant from a signal from a ideal fractal system and should vary for fractal system comprised of fractals and multifractals.

The determined characteristics (or quantitative parameters) are then displayed using a display 32 such as a cathode ray tube ("CRT"), liquid crystal display ("LCD") or video display or printed using a printer 34 such as laser printer, color plotter, or dot matrix printer. The determined characteristics displayed or printed may be a number, a series of numbers or a plot representative of the determined characteristics. These displays, plots, or numbers may then be used by the patient's doctor for diagnosis.

Figure 3:
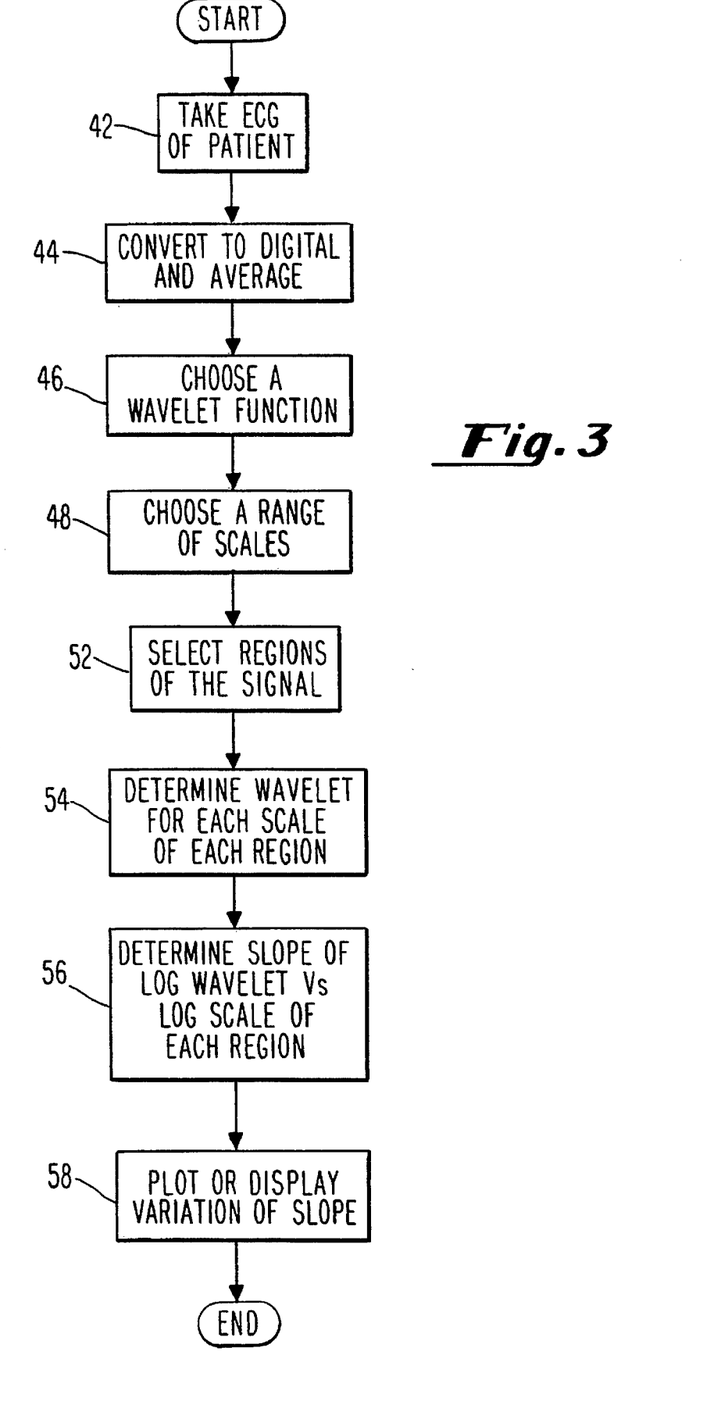
FIG. 3 is flow diagram of a preferred embodiment of a method of analyzing a signal from a fractal system in accordance with the present invention.

A detailed description of the operation of the preferred embodiment of the invention shown in FIG. 2 now will be described with reference to the flow diagram of FIG. 3. As shown in FIG. 3, the first step (42) in preferred embodiment of the invention for determining whether a patient is at risk for VT or sudden death and the like is to generate the ECG of the patient 22. In the preferred embodiment, the three signals X, Y and Z are generated by the electrocardiograph 24. These three signals, X, Y, and Z are then converted from analog to digital samples and averaged over many periods of the ECG in step 44. In the preferred embodiment of the invention, the analog signal is sampled at 1 millisecond ("msec") intervals to generate the digital samples representative of these signals of the ECG.

In step 46, an analyzing wavelet is selected for use in Equation 1 or 2. In the preferred embodiment of the invention, a "mexican hat" analyzing wavelet is used, where this analyzing wavelet is defined as:

$$(1-x^2)e^{\frac{-x^2}{T}} \quad (5)$$

Then a range of scales, a, is chosen in step 48 to be used in determining the wavelet transform of selected regions of the ECG signal 25. In a sample embodiment of the invention, 84 scales were used ranging from 0.004 seconds to 0.125 seconds. The regions of the ECG signal 25 used in the preferred embodiment of the invention to determine the characteristics of the fractal system 22 are then selected in step 52. In the preferred embodiment of the invention, regions were selected from a predetermined portion of the QRS of the ECG signal 25 using known techniques of determining where the QRS portion begins and ends in an ECG signal.

In the sample embodiment of the invention, regions were selected at every sample point, i.e., every 1 msec interval of the ECG signal 25. The portion of the QRS where the regions (or samples) were selected was the entire QRS except for the first 20 msec (first 20 samples or regions) and the last 20 msec (last 20 samples). An average QRS is generally from 80 to 100 msec in duration.

Now that the regions of the ECG for analysis, the scales, and the analyzing wavelet have been selected, in step 54 the wavelet transform is determined for each scale in each region in each signal X, Y, and Z of the ECG signal 25 using Equation 1 or 2. Then, in the preferred embodiment of the invention, the respective wavelet transforms for all the signals X, Y, and Z are combined and the log of the each combined wavelet transform for each scale and each region is determined at step 56.

Figure 4:
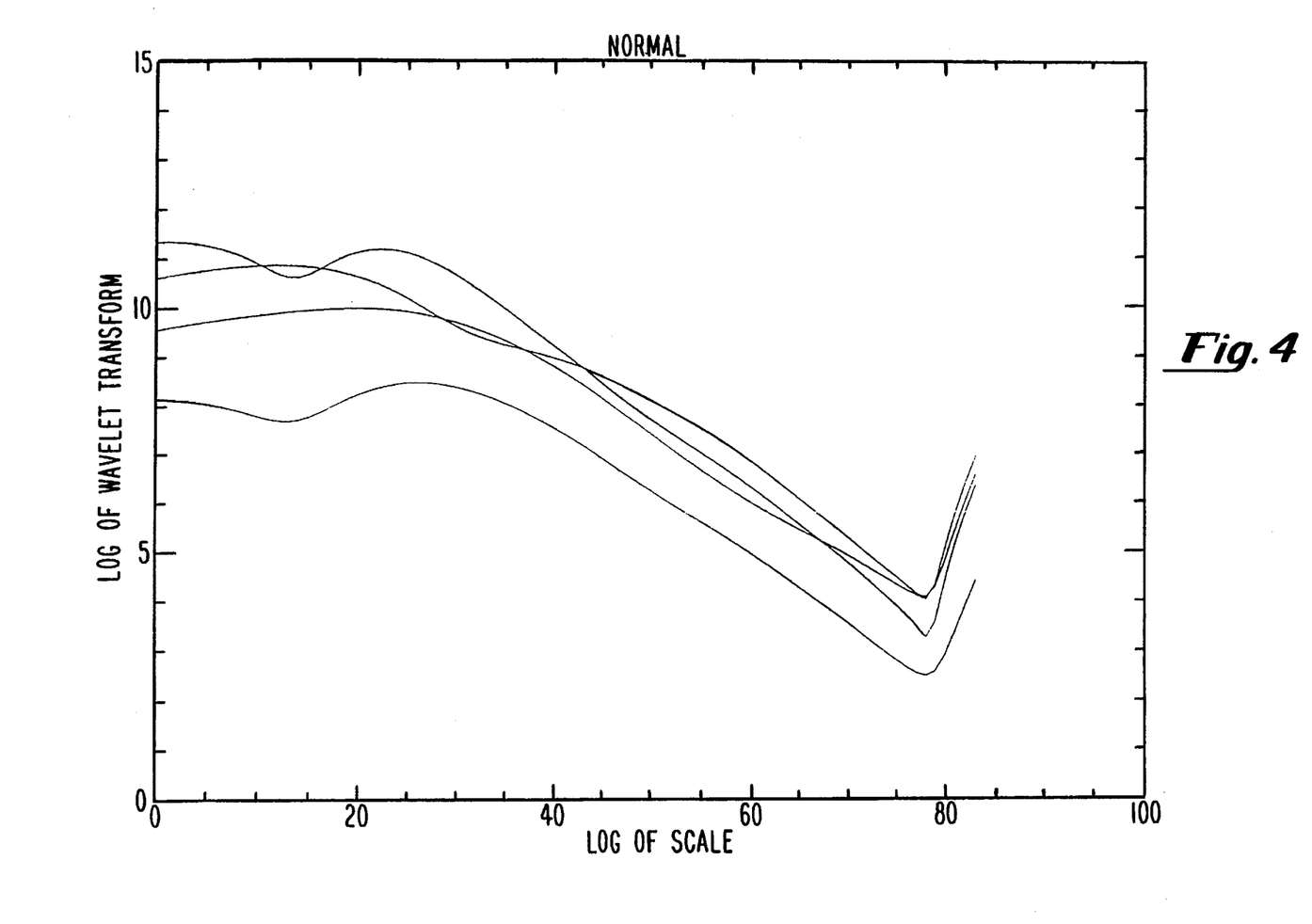
FIG. 4 is a plot of the log of the wavelet transform versus the log of the scales for four selected regions of the QRS of an ECG taken from a normal patient.
Figure 5:
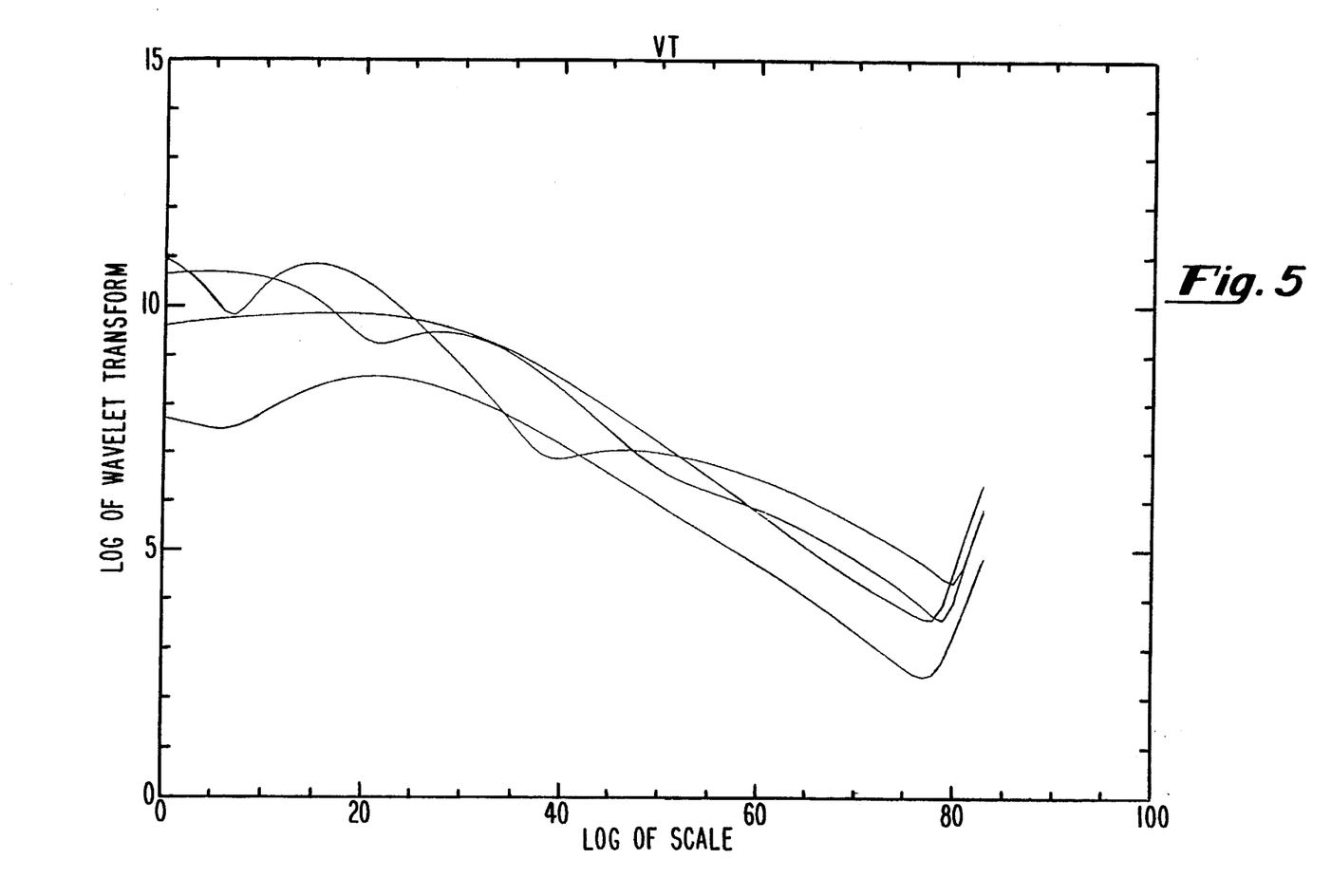
FIG. 5 is a plot of the log of the wavelet transform versus the log of the scales for four selected regions of the QRS of an ECG taken from a patient at risk for VT or sudden death.

In step 56, the slope of the log of the wavelet transform versus the log of the scale for each region is determined. In particular, the slope of the log of the scales versus the log of the absolute value of the corresponding combined wavelet transform for the three signals X, Y, and Z is determined. If the log of the wavelet transform versus the log of the scales is plotted (as shown in FIGS. 4 and 5), a linear portion of the curve for each region can be identified and used to determine the slope. For example, as shown in FIG. 4, the plot of the log of the wavelet transform versus the log of the scale is shown for four different regions (four curves) for a normal patient 22. The slope of each region is determined in the linear area of the respective curves, in this example, from the region of the scales from 40 to 60. Linear regression may be used to find the portions where the curve is linear.

Once the slopes are determined, the slopes are compared and the variations of the slopes are displayed or plotted at step 58. The display or plot could be a number representing the statistical variation or standard deviation of the slopes of the regions. Using linear regression as mentioned above, the slope of each region could be determined by the computer system 26 and stored in the RAM of the computer 26. Then the variance or standard deviation of all of the slopes of the selected regions could be determined. For example, this value could indicate whether the fractal structure of the heart conduction system of the patient 22 is above a predetermined threshold, and thus whether the heart is healthy or not. If the variance or standard deviation is large, then this value could indicate the presence of multifractals in the heart conduction system and thus the presence of heart disease or that the patient 22 is at risk for VT or sudden death. On the other hand, if the variance is low, it may indicate that the heart conduction system of the patient 22 does not contain multifractals and correspondingly, that the patient 22 is not at risk for VT or sudden death or that the patient 22 does not have heart disease.

The variance of the slopes may also be plotted as shown in FIGS. 4 to 7. FIGS. 4 and 5 are plots of the log of the wavelet transform versus the log of the scale for four regions or time points of the QRS. A different constant was added to each curve to minimize overlap among the four different curves. FIG. 4 represents the slopes for a normal patient 22. As can be seen from this figure, each of the four curves has approximately the slope in linear region of the curves, i.e., where the scale is from 40 to 60. FIG. 5 represents the curves of regions for a patient at risk for VT or sudden death. As can be seen from this figure, each of the four curves has a different slope, some which are not linear in the region of the log of the scales from 40 to 60. This plot clearly shows the greater variance among the slopes for a patient at risk for VT or sudden death versus a patient not at risk for VT or sudden death.

Figure 6:
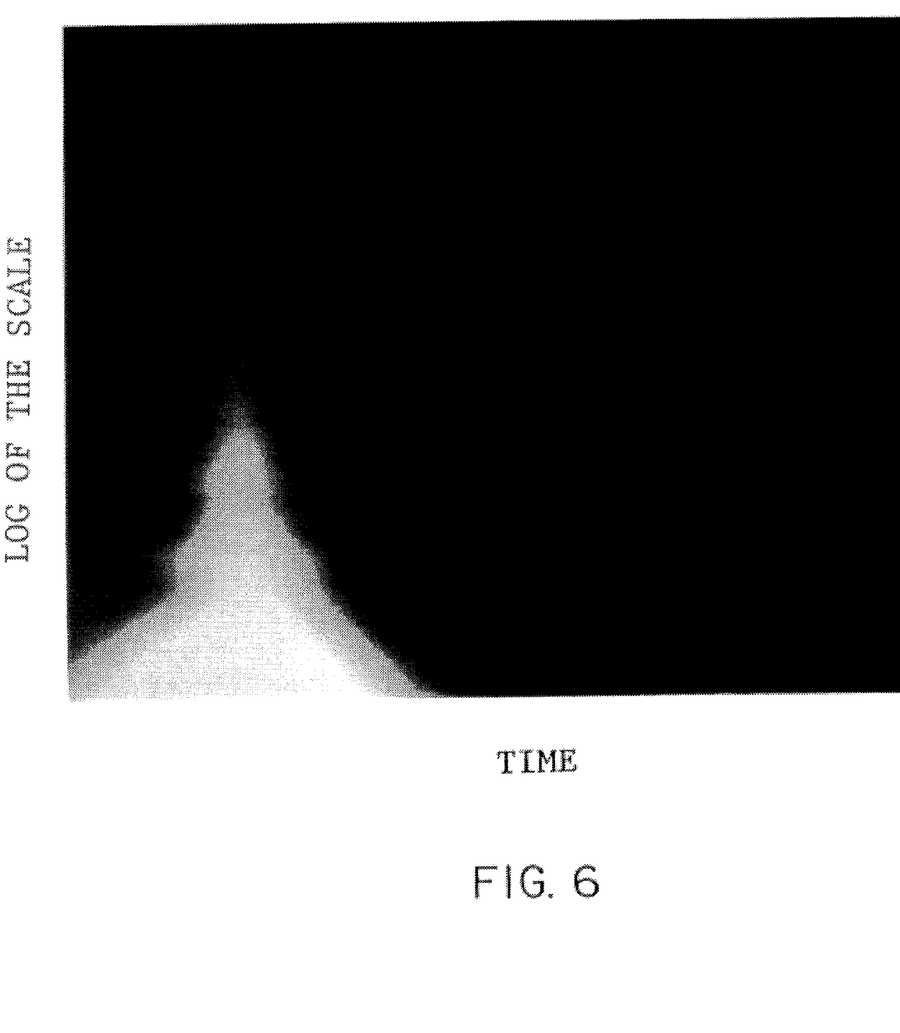
FIG. 6 is a gray scale plot of the amplitude of the wavelet transform for an ECG signal taken from a normal patient where the horizontal axis is time and the vertical axis is the log of the scale of the wavelet transform.
Figure 7:
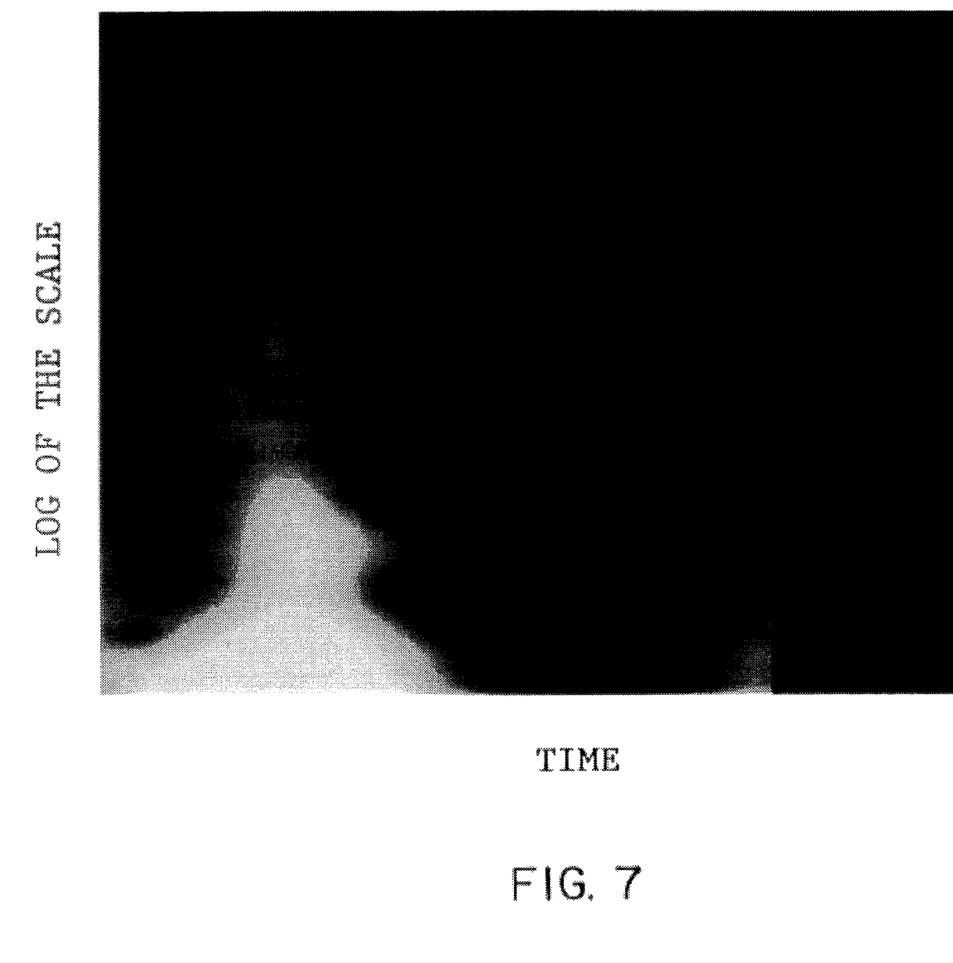
FIG. 7 is a gray scale plot of the amplitude of the wavelet transform for an ECG signal taken from a patient at risk for VT or sudden death where the horizontal axis is time and the vertical axis is the log of the scale of the wavelet transform.

FIGS. 6 and 7 are gray scale plots of the wavelet transform of a signal averaged ECG signal 25 of a normal patient 22 and a patient at risk for VT or sudden death. The analyzing wavelet used in the wavelet transform was a complex modulated Gaussian. The three orthogonal ECG signals, X, Y, and Z were analyzed separately. The vector amplitude of the wavelet transform is plotted in gray scales which go from white (high amplitude) to black (low amplitude). The horizontal axis is time and is 450 msec. The vertical axis is the scale used in the wavelet transform in logarithmic units. The large peak in the left portion of FIGS. 6 and 7 represents the QRS of the ECG signal 25. For the normal patient 22, as shown in FIG. 6, the transition between the gray scales, i.e., the change in the wavelet transform is smooth. For the patient at risk for VT or sudden death, the change in the wavelet transform is not smooth. These plots, FIGS. 6 and 7, also clearly show the greater variance between the slopes for a patient at risk for VT or sudden death versus a patient not at risk for VT or sudden death.

From the foregoing it can be seen that the present invention is directed to a method and system for evaluating characteristics of a signal derived from a fractal system such as the heart using wavelet functions and thereby to determine characteristics of the underlying fractal system. It is understood that changes may be made to the embodiments described above without departing from the broad inventive concepts thereof. For example, different wavelet analyzing functions may be used in place of the "mexican hat" analyzing function. In addition, different fractal systems besides the conduction system of a heart can be analyzed using the present invention. For example, any system that can be ideally represented by fractals can be evaluated by the present invention. One such system is financial markets or stocks markets. In other words, wavelet analysis can be applied to the stock market "ticker" signal to identify short term and long term trends. The present invention is then used to predict the behavior of the financial markets or stock markets based the variation of the slope of selected regions of signals generated by these systems.

Accordingly, this invention is not limited to the particular embodiments disclosed, but is intended to cover all modifications that are within the scope and spirit of the invention as defined by the appended claims.

What is claimed is:

1. A method of determining characteristics of a signal derived from a fractal system, comprising the steps of:

a) selecting a region of said signal for analysis which is known to be self affine;

b) performing wavelet analysis of the selected region to determine whether said region is indeed self affine during normal operation of said fractal system; and c) determining said characteristics of said fractal system as a function of whether the selected region is self affine.

2. A method for analyzing an electrocardiogram ("ECG") signal to determine whether a patient is at risk for ventricular tachycardia or sudden death, comprising the steps of:

a) selecting a region of the ECG signal for analysis;

b) performing wavelet analysis of the selected region of said ECG signal to determine whether said region is substantially self affine and exhibits no abnormalities or whether said region is not substantially self affine and exhibits abnormalities; and c) comparing a result of said wavelet analysis to a predetermined threshold to determine whether the selected region of said signal exhibits an abnormality representative of a risk for ventricular tachycardia or sudden death.

3. A method for determining whether a patient is at risk for ventricular tachycardia or sudden death, comprising the steps of:

a) using an electrocardiograph to generate an electrocardiogram ("ECG") signal of the patient;

b) selecting a region of the ECG signal for analysis;

c) performing wavelet analysis of the selected region of said ECG signal to determine whether said region is substantially self affine and exhibits no abnormalities or whether said region is not substantially self affine and exhibits abnormalities; and d) comparing a result of said wavelet analysis to a predetermined threshold to determine whether the selected region of said signal exhibits an abnormality representative of a risk for ventricular tachycardia or sudden death.

4. A system for determining characteristics of a signal derived from a fractal system, comprising:

a wavelet analysis system adapted to:

select a region of said signal for analysis which is generally self affine, perform wavelet analysis of the selected region to determine whether said region is indeed self affine during normal operation of said fractal system, and determine said characteristics of said fractal system as a function of whether the selected region is self affine; and means for indicating an output of said analysis system to an operator for a determination of said characteristics.

5. A system according to claim 4, wherein said indicating means is a printer.

6. A system according to claim 4, wherein said indicating means is a display device.

7. A system for determining whether a patient is at risk for ventricular tachycardia or sudden death, comprising:

an electrocardiograph adapted to generate an electrocardiogram ("ECG") signal of the patient; and a computer system adapted to:

select a region of the ECG signal for analysis, perform wavelet analysis of the selected region of said ECG signal to determine whether said region is substantially self affine and exhibits no abnormalities or whether said region is not substantially self affine and exhibits abnormalities, and compare a result of said wavelet analysis to a standard indicative of a normal ECG to determine whether the selected region of said signal exhibits an abnormality representative of a risk for ventricular tachycardia or sudden death.

8. A system according claim 7, wherein the computer system is adapted to:

convert the ECG signal of the patient to a digital signal;

select a wavelet function;

select a range of scales;

select a region of the digital signal for analysis;

perform wavelet analysis of the selected region of said digital signal using the selected wavelet function and the selected range of scales to determine whether said region is substantially self affine and exhibits no abnormalities or whether said region is not substantially self affine and exhibits abnormalities; and compare a result of said wavelet analysis to a standard indicative of a normal ECG to determine whether the selected region of said signal exhibits an abnormality representative of a risk for ventricular tachycardia or sudden death.

9. A system according claim 7, wherein the computer system is adapted to:

convert the ECG signal of the patient to a digital signal;

select a wavelet function;

select a range of scales;

select a region of the digital signal for analysis;

perform wavelet analysis of the selected region of said digital signal for each scale of the selected range of scales using the selected wavelet function to determine whether said region is substantially self affine and exhibits no abnormalities or whether said region is not substantially self affine and exhibits abnormalities; and compare a result of said wavelet analysis to a standard indicative of a normal ECG to determine whether the selected region of said signal exhibits an abnormality representative of a risk for ventricular tachycardia or sudden death.

10. A system according claim 7, where the computer system is adapted to:

convert the ECG signal of the patient to a digital signal;

select a wavelet function;

select a range of scales;

select a region of the digital signal for analysis;

perform wavelet analysis of the selected region of said digital signal for each scale of the selected range of scales using the selected wavelet function to determine the wavelet of each of the selected scales of the region;

determine the log of the wavelet of each scale of the selected scales of each region;

determine the log of each scale of the selected scales of the region;

compare a slope of the log of the wavelet of each scale of the selected scales of the region to the log of each scale of the selected scales of the region to determine whether said region is substantially self affine and exhibits no abnormalities or whether said region is not substantially self affine and exhibits abnormalities; and compare the result of said comparison to a standard indicative of a normal ECG to determine whether the selected region of said signal exhibits an abnormality representative of a risk for ventricular tachycardia or sudden death.

\* \* \* \* \*

UNITED STATES PATENT AND TRADEMARK OFFICE
CERTIFICATE OF CORRECTION

PATENT NO. : 5,471,991
DATED : December 5, 1995
INVENTOR(S) : Meir Shinnar

It is certified that error appears in the above-indentified patent and that said Letters Patent is hereby corrected as shown below:

Col. 1, line 63, after "Accordingly," insert --the--.

Signed and Sealed this

Twenty-third Day of July, 1996

Attest:

BRUCE LEHMAN

Attesting Officer    Commissioner of Patents and Trademarks